Figure 1:
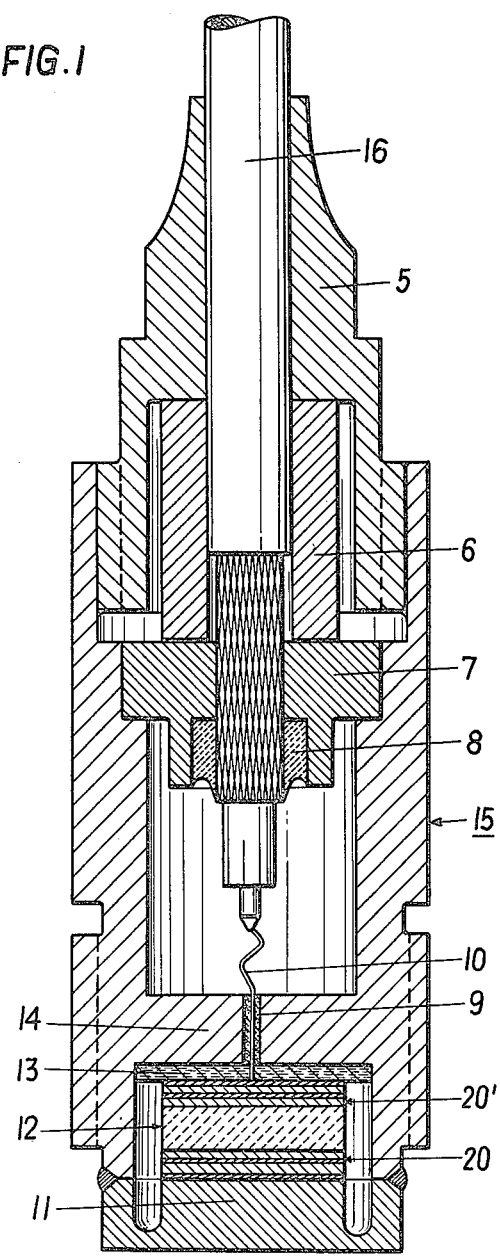

United States Patent [19]

Benes et al.

[11] 4,166,967

[45] Sep. 4, 1979

[54] PIEZOELECTRIC RESONATOR WITH ACOUSTIC REFLECTORS

[75] Inventors: Ewald Benes; Dieter Hammer, both of Vienna, Austria

[73] Assignee: Hans List, Graz, Austria

[21] Appl. No.: 843,215

[22] Filed: Oct. 18, 1977

[30] Foreign Application Priority Data

Oct. 19, 1976 [AT] Austria ..................... 7782/76

[51] Int. Cl.² .................................. H01L 41/10
[52] U.S. Cl. ......................... 310/338; 310/322; 310/334; 310/326; 310/329; 367/152
[58] Field of Search .............. 310/322, 323, 324, 325, 310/326, 334, 336, 337, 338, 329; 340/8 MM

[56] References Cited

U.S. PATENT DOCUMENTS

| | | | |
|---|---|---|---|
| 2,430,013 | 11/1947 | Hansell | 310/324 |
| 2,434,255 | 1/1948 | Bond et al. | 340/8 MM |
| 3,362,501 | 1/1968 | Lenahan | 310/334 |
| 3,979,565 | 9/1976 | McShane | 310/312 X |
| 4,016,530 | 4/1977 | Goll | 310/322 |

Primary Examiner—Mark O. Budd
Attorney, Agent, or Firm—Watson, Cole, Grindle & Watson

[57] ABSTRACT

A piezoelectric resonator, particularly for pressure, acceleration, temperature and load transducers, consisting of a resonator core having holding discs on its opposite sides, said holding discs being formed of solid body layers, said layers consisting alternatively of materials having strongly different acoustic impedance for unit cross-sectional area.

11 Claims, 3 Drawing Figures

PIEZOELECTRIC RESONATOR WITH ACOUSTIC REFLECTORS

The invention relates to a piezoelectric resonator, consisting of a resonator core having means to hold the core, in particular for transducer applications, for instance pressure, acceleration, temperature and load transducers. The resonator core normally consists of one or several monocrystal discs, however it also may be made of piezo ceramics with sufficient low losses.

Piezoelectric resonators, especially quartz crystals, are used in an increasing scale for transducers for various physical measured variables, as e.g. temperature, pressure, and mass loading, and also to stabilize vibrators. By use of piezoelectric driven mechanical resonators many advantages are attained in the named field of application. These advantages result from the highly attainable values of the resonator quality factor (Q-value), which values exceed the attainable quality factors of electric oscillatory circuits for some orders of magnitude.

The damping of the resonator is composed of the inner acoustic losses caused by the mechanical oscillations of the piezoelectric stimulated resonator core and the losses caused by the output of sound energy to ambiency or to the mounting support of the resonator respectively. For the demand of a high resonator quality factor the last mentioned losses were up to now reduced by running the quartz crystals in a high vacuum; and the holder of the resonator which served also as an electrode lead, was attached in lumps at points of the quartz crystal having a vanishing amplitude.

Using the aforementioned conventional arrangements it is impossible to make a resonator having both sufficient high quality and high mechanical rigidity at the same time without generating in homogeneous mechanical stress within the resonator core.

To avoid the above mentioned disadvantages there are provided holding discs at the opposite sides of the resonator core which are formed of solid body layers, the dimensions of said layers in the direction of propagation of the piezoelectric stimulated sound wave measuring according to the invention being an odd multiple of $\frac{1}{4}$, preferably $\frac{1}{4}$ of the length of the sound waves in the concerned layer corresponding to the resonance frequency of the resonator, and said layers consisting alternatively of materials having a strongly different acoustic impedance per unit cross sectional area. To simplify matters in the further description "specific acoustic impedance" will be used instead of "acoustic impedance per unit cross-sectional area."

By this holding arrangement, called "sandwich-holder", the resonator core is held on a large surface by the solid body layers. The layers function as transformation layers which make it possible to transduce the acoustic impedance of the medium outside of the holder to any required value.

By using alternating layers consisting of materials with strongly different specific acoustic impedance, according to the laws of physics, an extremely high or extremely low, respectively, acoustic termination impedance can be attained. Such a termination impedance gives use to a nearly nondissipative reflection of the sound wave produced by the resonator. The holding discs according to the invention act as "acoustic mirrors" and a high quality resonator with a rigid large surface holder is attained. The resonator core may consist in the usual way of a monocrystal piece of quartz, lithiumniobat or lithiumtantalat, but may also be built up by several of such crystal pieces. It also should be possible to use piezoelectric ceramics with sufficient low acoustic losses instead of piezoelectric monocrystals.

It may be advantageous for at least some of the layers to be built up in several plys using a material having equal acoustic impedance. At this arrangement each ply is formed of a single homogeneous material.

A further advantage may be attained by interposing additional layers, said layers measuring in the direction of propagation of the piezoelectric stimulated sound wave $\frac{1}{2}$, or an integer multiple of $\frac{1}{2}$, of the length of the sound wave in the concerned layer corresponding to the resonance frequency of the resonator.

According to another preferred embodiment of this invention the outmost layer of the holding discs consists of a material having a higher specific acoustic impedance as opposed to the adjacent layer. This enables the attainment of a resonator with a high quality factor using only a small number of layers.

According to the invention the odd-numbered and the even-numbered solid body layers of the holding discs may each be made of the same material, whereby a more simple production of the holder is possible.

For the use of the resonator as a pressure transducer according to a further embodiment of the invention a compensation layer is provided for temperature compensation of the resonance frequency. The compensation layer is adjacent to at least one of the surface layers standing perpendicular to the direction of propagation of the piezoelectric stimulated sound wave. The compensation layer measures in the direction of propagation of the piezoelectric stimulated sound wave $\frac{1}{2}$ or an integer multiple of half the wave length in the compensation layer and its temperature expansion coefficient is selected such that the resonance frequency is nearly independent of temperature influence.

According to another advantageous embodiment of the invention, using the resonator as a temperature transducer, the temperature expanding coefficients of the materials of the integral embodiment consisting of the resonator and the housing are selected such that temperature variations cause pressure variations at the resonator core, which amplify the temperature sensibility of the resonance frequency of the resonator core. The expansion coefficients of the materials used and the construction are advisably selected in such a manner that an intense pressure variation upon the resonator is the result of temperature variation.

The main advantage of the "sandwich-resonator" in its application as a transducer is the perfect homogeneous pressure strain of the resonator core. At the temperature transducer the large surface heat flow to the sensor and the high attainable temperature sensitivity is a further advantage. The pressure transducer shows further advantages as compared to the common resonator arrangements enabling a more simple construction, a substantial reduction of dimensions, and an increased pressure range.

Applying larger dimensions the L/4-layers may be made of sheet metal of foils or rod-shaped raw material. According to another feature of the invention the layers or plys of the holding discs may be deposited or made by galvanic means. In this case the expensive resonator housing may be omitted when using the "sandwich-resonator" for frequency stabilizing, for instance in electronic wrist watches, because the resonator then has not to be run at high vacuum. It is also possible to produce the holding discs, or the single L/4-layers, or the plys separated from the resonator core by thin film deposition or galvanic means.

According to a further embodiment of the invention the adhesion of the layers or the plys respectively among one another and/or to the resonator core may be increased by depositing, compared to the dimensions of the layer, a very thin adhesion film. This can cause a reduction of the acoustic losses at the interface between the layers or plys. As a material for the adhesion film gold may be used. As a last feature of the invention good adhesion of the layers or the plys among one another and/or to the resonator core can also be attained by means of epitaxy.

Figure 2:
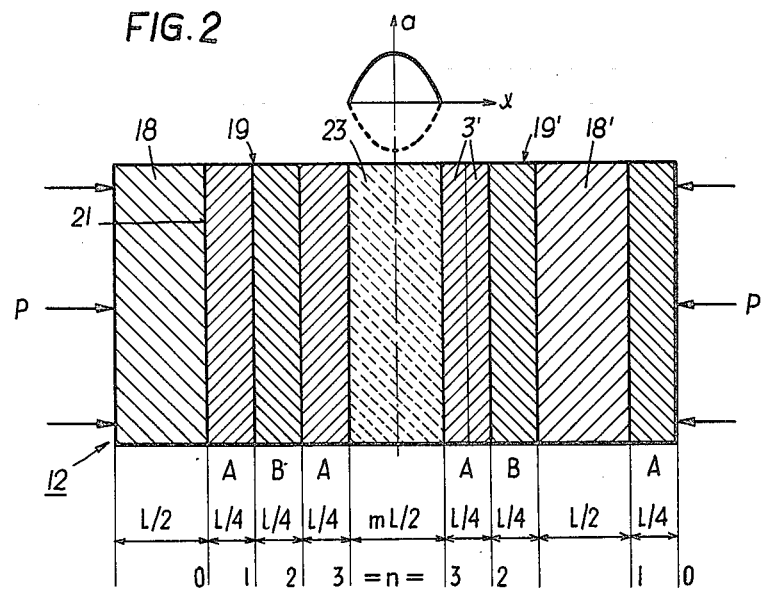
Figure 3:
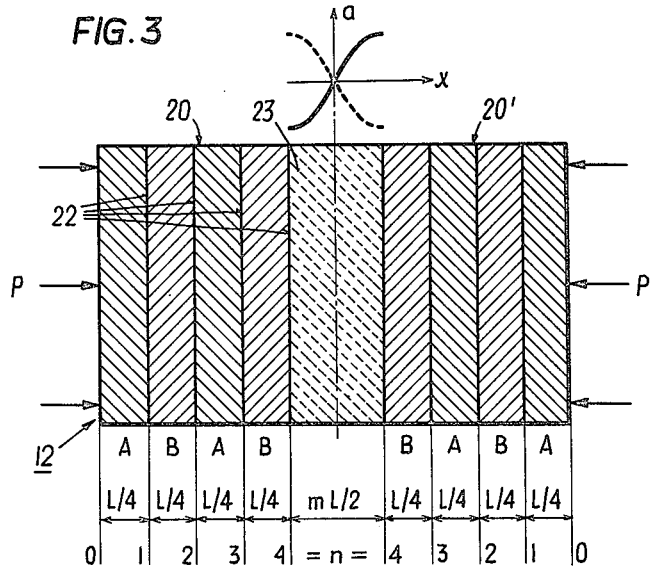

The invention will be hereinafter more specifically explained with reference to exemplary embodiments depicted in the accompanying drawings, wherein:

FIG. 1 is an axial section of a pressure transducer;

FIGS. 2 and 3 each show a detail of FIG. 1 turned around 90 degrees in different embodiments.

With reference to the embodiment depicted in the drawing the pressure transducer comprises a piezoelectric "sandwich-resonator" 12. The sandwich-resonator 12 is held between the membrane part 11 and the housing 14. Membrane part 11 and housing 14 are made of stainless steel. The membrane thickness measures an integer multiple of L/2, and so does the housing 14 in the range of the seat of the resonator 12. On the upper side of the resonator 12 a L/2 thick insulating piece 13, made of quartz, is interposed between the holder disc 20' and the housing 14. The acoustic impedance of the surrounding medium is immediately joined to the first two L/4-layers of the sandwich-resonator because the pressure transmission of the sandwich-resonator occurs over housing surfaces measuring L/2 or a multiple of L/2 respectively. The above data is taken as a basis for the following description of the schematic representation of the invention. The insulation tubule 9 serves as an insulation for the electrode lead 10 against the housing 14. The insulated lead is directed to the holding disc 20', which serves at the same time as an electrode, and is connected to the inner lead of the teflon covered coaxial cable 16. The shielding of the coaxial cable 16 is connected via soft solder 8, traction relief disc 7, housing 14 and membrane part 11 to the holding disc 20, which also serves as an electrode. The traction relief disc 7, made of brass, is pressed to the housing 14 by means of the brass spacer 6 and the cover piece 5. The housing 15 consists of the housing body 14, the insulating piece 13, the membrane part 11 and the cover piece 5.

The sandwich-resonator 12 itself is shown schematically in FIGS. 2 and 3 respectively on a larger scale. FIG. 2 shows the case where the number N of the L/4-layers 1-3 in each holding disc 19, 19' is odd. FIG. 3 shows the case where the number N of the L/4-layers in each holding disc 20, 20' is even (in the embodiment according to FIG. 1 the number of layers is N=4). The number m indicates at which harmonic the resonator core is operated (in the exemplary embodiment m=5). The resonator core 23 in the exemplary embodiment is a monocrystal disc with a thickness of m.L/2. L/4-layer A having an acoustic impedance as high as possible (in the exemplary embodiment the layer A is made of tungsten), and L/4-layer B having an acoustic impedance as low as possible (in the exemplary embodiment the layer B is made of a magnesium-base alloy of 7.5% Aluminium and 1.1% tin) are positioned as shown in FIG. 2. P designates the pressure exerted on the sandwich-resonator 12. For further illustration of the function principle the amplitude trace for the oscillation m=1 is shown above the resonator core. The mechanical amplitude of the resonator is designated by a, and the distance from the vertical axis of symmetry by x. Referring to FIG. 2 a compensation layer 18 of thickness L/2 is adjacent to the outer surface 21 of the holding disc 19, and there is an intermediate layer 18' of thickness L/2 between the layers 1 and 2 and a further layer 3 built up by two plys 3'. FIG. 3 also shows the arrangement of the very thin adhesion films 22. What follows is a description of the procedure for the dimensioning of the sandwich-resonator. The transforming effect of the first L/4-layer can be represented by the equation $$Z_1 = Z_A^2/Z_o$$

with $Z_o$ . . . specific acoustic impedance of the medium surrounding the holder $Z_A$ . . . specific acoustic impedance of the first L/4-layer $Z_1$ . . . impedance generated by the said transformation layer The following equations represent the impedance generated by the series arrangement of N L/4-layers:

$$Z_N = \frac{Z_A^{N+1}}{Z_B^{N-1} \cdot Z_O}, N \text{ uneven}$$

$$Z_N = \frac{Z_B^N}{Z_A^N} \cdot Z_O, N \text{ even}$$

The perceptual sandwich-resonator is suitable for all known modes of oscillations. The resonator core may be operated as a longitudinal thickness vibrator (stimulation of a longitudinal stationary soundwave perpendicular to the surface with the largest extension), as a thickness shear vibrator (stimulation of a transversal sound wave perpendicular to the surface with the largest extension), and also as a so-called surface-shear-vibrator, a bending vibrator, a torsional vibrator and a rod-shaped longitudinal vibrator (stimulation of a longitudinal wave in the longitudinal direction). The L/4-layers have to be dimensioned according to the kind of the stimulated oscillation for the true phase velocity in each case. Into the equations for the evaluation of the specific impedance $$Z_A = D_A \cdot n_A \text{ resp. } Z_B = D_B \cdot n_B$$

for $n_a$ or $n_B$, respectively, the phase velocity of the longitudinal, transversal, bending, torsional or extensional wave in the considered medium has to be inserted ($D_A$, $D_B$ are the respective densities of the concerned materials).

The pressure transducer according to the exemplary embodiment has a quartz crystal run as a longitudinal thickness vibrator. The respective holding discs 19, 19' and 20, 20' are metallic layers and therefore they can be used as electrodes. For pressure transducers with a small required diameter it may be more advantageous to construct the resonator as a bending, torsional or rod-shaped longitudinal vibrator. In that case the L/4-dimension generally will lie in the longitudinal direction of the layers and the electrodes will be attached separately at the resonator monocrystal. The resonator quality factor which can be attained by the diverse numbers of L/4-layers can be calculated using the already mentioned equations and the equation for the transmission rate of the sandwich cover $$T = 1 - (Z_N - Z_Q)^2/(Z_N + Z_Q)^2$$

whereby $Z_Q$ is the specific acoustic impedance of the resonator monocrystal in the direction of propagation of the stimulated acoustic wave.

The following table represents the theoretical values with the inner acoustic losses, not including $Z_N$, and the theoretically yielded quality values $Q_N$ for the pressure transducer according to the exemplary embodiment ($Z_A = Z_W = 100,75 \cdot 10^5 \text{g/cm}^2\text{s}$, $Z_B = Z_{MgALZn} = 10,04 \cdot 10^5 \text{g/cm}^2\text{s}$).

| N | $z_N(\text{g/cm}^2\text{s})$ | Q |
|---|---|---|
| 1 | $1,02 \cdot 10^4$ | 193 |
| 2 | $9,93 \cdot 10^2$ | 331 |
| 3 | $1,02 \cdot 10^{11}$ | 19 500 |
| 4 | $9,86 \cdot 10^0$ | 33 300 |
| 5 | $1,03 \cdot 10^{13}$ | 1 960 000 |
| 6 | $9,79 \cdot 10^{-2}$ | 3 350 000 |
| 7 | $1,04 \cdot 10^{15}$ | 197 000 000 |

For $N=5$ already a quality factor results comparable to that of a conventional supported high accuracy vacuum quartz member. As specific impedance $Z_o$ was taken as $1.10^5 \text{g/cm}^2\text{s}$, in practice it is even better. Generally the support is surrounded by a gaseous or fluid medium, therefore $Z_o$ vanishes totally for transverse sound waves.

In practice the attained quality factors are somewhat lower than that shown in the table due to the inner acoustic losses in the L/4-layers and the losses in the interface between the layers. These additional losses are not of great significance when the resonator monocrystal is operated at a higher harmonic, because this type of resonator has in the direction of the piezoelectric stimulated sound wave relative to the holding discs, larger dimensions. That is the reason why the exemplary embodiment m was chosen as 5.

We claim:

1. A piezoelectric resonator for pressure, acceleration, and temperature sensors comprising a resonator core having holding discs on its opposite sides, said holding discs being formed of solid body layers, the dimensions of said layers measured in the direction of propagation of the piezoelectric stimulated sound wave each are ¼ or an odd multiple of ¼ of the length L of the sound waves in the respective layer corresponding to the resonance frequency of the resonator core, said holding discs being acoustic reflectors, said layers consisting alternatively of materials having significantly different specific acoustic impedance.

2. A piezoelectric resonator according to claim 1, wherein at least some of said layers are built up of several plys using a material having equal specific acoustic impedance.

3. A piezoelectric resonator according to claim 1, further comprising additional layers being interposed, the dimensions of said layers measured in the direction of propagation of the piezoelectric stimulated sound wave are ½ or an integer multiple of ½ of the length L of the sound wave in the respective layer corresponding to the resonance frequency of the resonator core.

4. A piezoelectric resonator according to claim 2, further comprising additional layers interposed between said holding discs, said layers having dimensions measured in the direction of propagation of the piezoelectric stimulated sound wave ½ or an integer multiple of ½ of the length L of the sound wave in the respective layer corresponding to the resonance frequency of the resonator core.

5. A piezoelectric resonator according to claim 1, wherein the outmost layer of the holding discs consists of a material having a higher specific acoustic impedance than the adjacent layer.

6. A piezoelectric resonator according to claim 1, wherein the odd-numbered and even-numbered solid body layers of the holding discs are each formed of the same material.

7. A piezoelectric resonator according to claim 1, wherein said layers of the holding discs are deposited.

8. A piezoelectric resonator according to claim 1, wherein the layers of the holding discs are made by galvanic means.

9. A piezoelectric resonator according to claim 1, wherein the adhesion of the layers among one another and to the resonator core is increased by depositing an adhesion film having a negligible thickness compared to that of said layers.

10. A piezoelectric resonator according to claim 3, wherein the adhesion of the layers among one another and to the resonator core is increased by depositing an adhesion film having a negligible thickness compared to that of said layers.

11. A piezoelectric resonator according to claim 1, wherein adhesion of the layers among one another and to the resonator core is attained by means of epitaxy.

* * * * *